(12) United States Patent
Jacobson

(10) Patent No.: US 11,197,680 B2
(45) Date of Patent: Dec. 14, 2021

(54) BONE CLEANING TOOL

(71) Applicant: Daniel R. Jacobson, Chicago, IL (US)

(72) Inventor: Daniel R. Jacobson, Chicago, IL (US)

(*) Notice: Subject to any disclaimer, the term of this patent is extended or adjusted under 35 U.S.C. 154(b) by 210 days.

(21) Appl. No.: 16/532,101

(22) Filed: Aug. 5, 2019

(65) Prior Publication Data

US 2019/0350598 A1 Nov. 21, 2019

Related U.S. Application Data

(63) Continuation-in-part of application No. 15/973,483, filed on May 7, 2018, now Pat. No. 10,368,883, which is a continuation of application No. 14/704,616, filed on May 5, 2015, now abandoned.

(60) Provisional application No. 61/988,818, filed on May 5, 2014.

(51) Int. Cl.
*A61B 17/16* (2006.01)

(52) U.S. Cl.
CPC ...... *A61B 17/1659* (2013.01); *A61B 17/1615* (2013.01); *A61B 17/1671* (2013.01)

(58) Field of Classification Search
CPC .................. A61B 17/1615; A61B 17/1659
See application file for complete search history.

(56) References Cited

U.S. PATENT DOCUMENTS

| | | | | |
|---|---|---|---|---|
| 4,197,645 A | * | 4/1980 | Scheicher | A61C 8/0043 433/128 |
| 5,562,673 A | * | 10/1996 | Koblish | A61F 2/4657 606/80 |
| 5,665,091 A | * | 9/1997 | Noble | A61B 17/1659 606/79 |
| 2005/0089817 A1 | * | 4/2005 | Kuhn | F16C 35/067 433/114 |
| 2007/0250067 A1 | * | 10/2007 | Schmieding | A61B 17/1617 606/96 |
| 2015/0366568 A1 | * | 12/2015 | Victor | A61B 17/1659 606/81 |

* cited by examiner

*Primary Examiner* — Christian A Sevilla
(74) *Attorney, Agent, or Firm* — BrainSpark Associates, LLC

(57) ABSTRACT

The present invention is directed to systems, methods, tools and surgical procedures that provide for improved, faster and/or more efficient methods for cleaning bone of soft tissue in preparation for use in bone grafting and surgery, including specific applications particularly useful in fusion procedures and/or other surgeries of the lumbar, cervical, and/or thoracic spine and/or other anatomical locations, desirably allowing for faster and complete healing.

10 Claims, 12 Drawing Sheets

BONE CLEANING TOOL

CROSS-REFERENCE TO RELATED APPLICATIONS

This application is a continuation-in-part of U.S. patent application Ser. No. 15/973,483, entitled "Bone Cleaning Tool," filed May 7, 2018, which is a continuation of U.S. patent application Ser. No. 14/704,616, entitled "Bone Cleaning Tool," filed May 5, 2015, which claims priority from U.S. Provisional Patent Application No. 61/988,818 filed May 5, 2014, entitled "Bone Cleaning Drill Bit," the contents of which are each hereby incorporated herein by reference in their entireties.

TECHNICAL FIELD OF INVENTION

The invention relates to systems, methods, tools and surgical procedures for denuding bone for bone bed preparation and/or preparing autograft bone for bone graft implantation into the body during bone grafting surgery, which can be used in a variety of anatomical locations within a patient. In various embodiments, the disclosed bone cleaning tool and related methods of use can be particularly useful in specific applications such as bone grafting and/or fusion surgery, including spinal fusion procedures and/or other surgery of the lumbar, cervical, and/or thoracic spine.

BACKGROUND OF THE INVENTION

During the course of spine fusion surgery, bone from spinous processes, laminae, facets and/or iliac crest are removed from a patient and are often reimplanted as autograft in increasingly numerous ways, typically to promote fusion of or other repairs to the patient's bones. In order to achieve bone fusion or osteogenesis, there will desirably be a bone to bone contact surface between the host bone and the bone graft. To achieve such a contact surface, soft tissue normally found on bone, such as periosteum, tendon, muscle, ligament and fibrous tissue will be removed from the contact point of both the host and graft bone. It has been well documented in the clinical literature that that intervening soft tissue hinders, if not totally prevents the connection of bone cells. Such impedance or prevention of the passage of the bone cells may cause the fusion procedure to fail thereby resulting in a negative impact on the health of the patient. One well known complication of spine fusion surgery is pseudoarthrosis, which can occur when a patient's vertebral segments fail to fuse together in a desired manner, often leading to back pain, instability, and need for further surgery. Even if a given fusion procedure is successful, the process may take a year or more for completion, and during this time (or for varying periods afterwards) the patient often experiences resultant pain and disability. There are many expensive methods, devices, biologics, and allografts currently commercially available that claim to improve the rate and/or quality of fusion in a surgical procedure.

Autologous bone graft refers to the removal of bone from one location in a patient and subsequently placed in the same and/or another location in the same patient. This type of bone graft is commonly called an autograft, and one major factor contributing to a successful and rapid fusion using autograft is "bone quality." The quality of bone that is prepared, removed, processed and reimplanted as autograft is often highly dependent on the techniques and experience of an individual surgeon, as well as the surgical technologist's skill level. Before bone can be reimplanted into a patient, the surgeon or surgical technologist will desirably clean the bone of connective tissues, and prepare the bone for fusion in various ways. Current methods of cleaning of the bone prior to reimplantation can include manually scraping the bone with various periosteal elevators, curettes, rongeurs, cautery tools and other multi-purpose tools. Typically, the muscles are stripped away from the bone using cautery and Cobb elevators. Soft tissue is partially removed with large rongeurs, and various portions of the bone are curetted. Depending upon the type of surgical procedure and type of surgical access (i.e., open, less-invasive and/or minimally-invasive approach paths), the spinous processes may be cut and the cut bone given to an assistant or technologist. Similarly, laminae and/or facets can be drilled (often with significant loss of bone stock) and may be rongeured, with small bone pieces given to the technologist, who may proceed to use fine rongeurs to remove any remaining soft tissue from the saved bone. This type of bone preparation and cleaning can be a tedious and time-consuming process. Prior to reimplantation, the harvested bone is then cut into small pieces, either manually with rongeurs, or mechanically (i.e., with a bone mill).

In many cases, the current bone cleaning process is often, tedious, difficult, incomplete, and/or time consuming resulting in (1) incomplete or inadequate bone graft preparation that may lead to delayed and inadequate fusion or healing, (2) incomplete or inadequate bone bed preparation that may lead to delayed and inadequate fusion or healing, (3) the use of undesirable bone graft, especially where it incorporates and/or is utilized with attached small tissue, (4) the discarding of good bone stock because it is difficult or impossible to separate from associated soft tissue, (5) an increase in the occurrence of pseudoarthrosis, or (6) failure of the surgical procedure. In all cases, these results may be suboptimal.

To compound the existing problems described above, the surgeons and/or surgical technologists typically use a combination of general purpose or various other cutting tools to prepare and remove autograft tissues. The tools that are typically used can include general multi-purpose tools that may be designed for proper bone removal, but are not intended and/or well suited to remove soft tissue. Such general multi-purpose tools can include rongeurs, curettes, periosteal elevators, drill bits, burrs and other tools. For example, currently used drill bits and burrs could be used to clean bone, but these are designed to cut, ream, or grind away bone, and are not typically intended to remove soft tissues while maintaining optimal fusion bone yield. Using generalized multi-purpose tools to prepare and remove the autograft can yield a wide variety of disadvantages, including (1) low autograft bone yield, (2) disposal of bone autograft because the bone graft may be too strongly attached to connective tissue for adequate or timely removal for the operation, (3) poor tool strength and material/bone build-up because it may not be used for its intended purpose, (4) multiple tool exchanges (and additional time for the surgeon) be may be required to accomplish preparation of a given anatomical structure of the patient, (5) loss and/or contamination of useable bone material where tool linkages, lubricants and/or coolants prevent collection and utilization of removed material, (6) difficulty in collecting removed bone material from cutting surfaces and/or tool voids, and/or (7) loss of bone from mishandling during the course of cleaning the bone.

Pre-existing devices for denuding, decorticating and shaping bone generally incorporated one of six basic design elements; fluted bone burrs, saw blades with various tooth configurations, bone cutting rongeurs, scalpels, cautery devices and wire-bristle type brushes. While some such instruments have been used to remove soft tissue and shape bone, each is functionally limited in providing an effective means to remove soft tissue from bone.

As an example of prior art, bone burrs have been commonly used to decorticate autografts and allografts. However, to remove soft tissue from bone, bone burrs require significant force and high speed rotation of the burr. The force applied, as well as the high speed rotation of the burr, typically generates heat at the contact point where the burr is placed on the bone. Such heat increases the potential for the onset of thermal necrosis. Additionally, such prior art devices commonly require the application of water during its use to reduce the heat build-up. The use of water can significantly decrease the visibility within the operative area and thereby creates a potential surgical problem.

An earlier prior art device, the bone saw blade, was designed to cut bone in a straight line. Though the saw blade can effectively cut bone, it is ineffective and impractical to use a saw blade to remove layers of soft tissue from bone, as the saw is typically unable to differentiate between the types of tissue(s) it is cutting. Attempts at such removal generally resulted in loss of bone stock and very little removal of the soft tissue. Further, the use of saw blades does not provide a means to easily contour round bone or bone grafts.

An example of a prior art manual instrument device is represented by the bone cutting rongeur. This instrument can be used to remove soft tissue from bone and has been used for this purpose. Such use however, requires that the jaws of the device bite into the bone itself and thereby typically remove bone material in the process of removing soft tissue. The use of such a device is both time consuming and ineffective when small autograft or allograft are being used, and it is difficult to follow the contours or curved surfaces with rongeurs. Additionally, when bone cutting rongeurs are used, the volume of bone loss is significantly higher than with the current invention.

While not designed for use as a soft tissue removal device, the electro-cautery device can remove soft tissue as it effectively burns soft tissue away from bone. However, this device creates a significant amount of heat at the contact point of the cautery tip on the bone. Such large amounts of heat generation increase the potential of terminal necrosis at the bone contact point. Prior art devices used to remove soft tissue, decorticate and or shape bone, do not allow sufficient control of the amount of soft tissue removed as compared to the amount of bone removed or the device creates significant heat at the bone/device interface, thereby increasing the potential for a negative clinical result.

Another prior art device for soft tissue removal includes a wire-bristle type rotary cutter, such as disclosed in U.S. Pat. No. 5,733,288, the disclosure of which is incorporated herein by reference in its entirety. While wire-bristle rotary cutters are disclosed as being capable of separating soft tissue from underlying bone, the wire bristles will often very quickly fatigue and fracture in contact with the underlying bone surface, potentially ejecting the fractured wire outward in a manner which makes such brushes highly undesirable for use in surgical procedures. Moreover, the bristles can also easily remove hard and/or bony tissues in an indiscriminate manner, which is undesired in many instances. In addition, the high rotational speed of wire-bristle rotary cutters can easily generate excessive heat on the bone surface, and this rotation further typically renders such devices incapable of retaining any significant amount of morselized tissue and/or bone fragments, as the centrifugal force generated by such rotation will throw such fragments outward of the wire-bristle fibers.

As a result, an improved specialized tool may be desirable for surgeons and/or surgical technologists for autograft preparation and bone removal, allowing for efficient and effective removal of soft tissue(s) from host bone without removing significant quantities of the bone stock itself.

SUMMARY OF THE INVENTION

In various embodiments, a bone and soft tissue drill bit and/or tool (i.e., a bone cleaning rotary tool or "bone cleaning tool") may be used individually (as a single tool) and/or as an attachment to a commercially available high-speed surgical drill or custom high speed surgical drill. The commercial surgical drill may be of a type normally used in the surgical theatre, which reduces the need for additional equipment in the operating room. Furthermore, the head of the "bone cleaning tool" may incorporate into its design various biocompatible materials of differing shapes and dimensions such that, when applied to soft tissue connected to bone, the soft tissue can be removed in a desired manner and/or at a desired rate thoroughly while leaving the bone substantially intact. In various embodiments, disclosed devices and methods can facilitate the removal of soft tissue from human bone (1) without excessive heating of the bone, (2) without removal of significant amounts of the bone stock, and (3) in a significantly decreased time and improved efficiency as compared to other currently-available devices for preparing allograft bone and/or bone beds.

In various exemplary embodiments, the bone cleaning tool may be used in situ, prior to removal of the bone from the harvest site. By facilitating the separation and/or cleaning of bone from other soft tissues in situ, which can be desirably accomplished while the bone is still attached in an original position within the patient anatomy (where desired), the intact bone is desirably well-anchored to the anatomical site (reducing and/or obviating the need to hold or otherwise secure the bone during the preparation procedure), and the intact bone portion that is eventually removed from the patient can be substantially and/or completely "cleared" of any soft tissues, such that the surgeon or technologist does not need to spend effort and time to clean the bone, as well as assist with the handling of smaller-sized bone graft pieces. In this manner, the various tools and techniques described herein can result in better quality fusion bone, and higher fusion bone yield by significantly reducing disposal of good bone stock simply because it is attached to soft tissue structures that are difficult or impossible to remove.

In some embodiments, an improved bone cleaning tool may be provided with a guard or other features to inhibit removal of certain anatomical features and/or tissue types. In one embodiment, a guard may be positioned over the head and/or shaft of the bone cleaning tool to minimize airborne debris from use of a high-speed drill.

In various other alternative embodiments, an improved bone cleaning tool or other surgical tool may be designed to incorporate a double or triple helix flute configuration. The double or triple helix flute bone cleaning tool may be desirous for a wide variety of reasons, which could include advantages due to increased tool strength, or the tool may incorporate a fewer or greater number, shape, thickness and/or length of tubular projections, spines or other protrusions to remove soft tissue, and/or the bone cleaning tool may incorporate design features that can provide a unique pathway and/or debris retention feature(s) for bone and/or soft tissue material egress and/or containment/storage.

In various embodiments, a double or triple helix flute design may include specialized cutting surfaces, shapes, channels, and/or configurations that may provide a variety of features, including improvements in flute strength and/or cutting capabilities. For example, one embodiment incorporating a double or triple helix flute design may include a gutter, channel and/or trench where a plurality of spines may be placed in various locations throughout the flutes to prevent and/or reduce any yielding and/or rotation of the material, avoid deflection of the spines and/or direct collection of removed material in a desired manner. In various embodiments, one or more surfaces of one or more helixes may include a cutting or abrading surface on a leading or trailing edge of the helical surface, which may be in addition to the various spined surfaces described herein.

In other alternative embodiments, an improved bone cleaning tool may include design features such as spines and/or protrusions (or indentations, in other embodiment) that may include a plurality of shapes and/or configurations. The shapes and configurations of the spines may be short, long, wide, triangular, square, spherical, curved, rounded, and/or a combination thereof. Such a variety and/or plurality of shapes and/or configurations may be desirable based on whether the surgeon and/or surgeon technologist may want gross and/or fine soft tissue and/or bone removal, and/or to increase and/or decrease "splatter" for various reasons. In addition the plurality of shapes and/or configurations may be positioned on the surface of the bone cleaning tool uniformly or non-uniformly.

In various other alternative embodiments, an improved bone cleaning tool may be provided with spines or other features that may include independent bone cutting surfaces on one of more of the spine or other feature surfaces. The cutting surfaces may be designed with a plurality of shapes and configurations to accommodate the type of cutting desired by the surgeon and/or surgeon technologists, and selective activation of such cutting surfaces may be accomplished by a variety of techniques, including by reorienting of the bone cleaning tool and/or cutting surfaces relative to the soft tissue/bone and/or reversing rotation of the drill or other actuating tool attached to the bone cleaning tool. Such shapes and configurations of the cutting surfaces may include shapes or configurations that may allow and/or facilitate the grasping, pinching, cutting and/or severing of a specific type of target soft tissue and/or bone material there between. Furthermore, the shapes and/or configurations of the cutting surfaces may also have sharpened, beveled, and/or tapered cutting surfaces to sever, cut and/or grind the specific targeted bone or soft tissue, and/or accomplish whatever gross and/or fine cutting may be desired.

In various other alternative embodiments, an improved bone cleaning tool may be designed with spines including a variety of flexible or non-flexible materials, or various combinations thereof. Desirably, the spines can incorporate a plurality of surfaces that, when orientation and/or rotation of the bone cleaning tool is altered (i.e., by reversing the drill, for example), present a different cutting and/or abrading feature to the tissue(s) of interest. For example, a bone cleaning tool may be constructed that removes soft tissue from underlying bone in a forward direction, but which cuts, shapes and/or removes bone when operated in a reverse direction. Similarly, a bone cleaning tool may be constructed that removes gross amounts of soft tissue from underlying bone in a forward direction, but which cuts, shapes and/or removes lesser amounts of soft tissue from underlying bone when operated in a reverse direction.

In other alternative embodiments, an improved bone cleaning tool may be designed with different shapes and configurations to access various spacing, including small spaces up to large spaces, and/or different contoured bone surfaces. For example, the improved bone cleaning tool may be conically shaped allowing the surgeon and/or surgeon technologist to use the tip of the improved bone cleaning tool to access small spaces and/or under edges or create shapes or channels, which may include different cutting and/or shaping surfaces on the conical section as compared to other section(s) of the bone cleaning tool. The surgeon and/or surgeon technologist may advance the conically shaped bone cleaning tool portion to access larger spaces with the larger diameter, which may incorporate lesser or greater cutting features, if desired. Furthermore, the radiused perimeter may be designed to access, cut, grind, or smooth contoured bone and/or soft tissue, should it be desired.

In other alternative embodiments, an improved bone cleaning tool may be designed to include a plurality of apertures. The plurality of apertures may be positioned uniformly, non-uniformly, symmetrically, non-symmetrically, recessed from the outer diameter, raised from the outer diameter, and/or may have cutting edges on an outer, medial and/or inner surface(s), which may include an abrading surface on an outer surface of the tool (i.e., between apertures). In various embodiments, one or more apertures could include one or more outwardly extending cutting surfaces, in a manner similar to the cutting surfaces within apertures of a cheese grate or microplane. In various embodiments, the cutting edges/surfaces could be contained within the apertures and/or recessed inside or and/or below the apertures, if desired. In various embodiments, two or more cutting surfaces having differing shapes, sizes and/or modes of cutting action could be incorporated into a single individual aperture.

In other alternative embodiments, the improved bone cleaning tool may be available as separate and individual tools, and/or multiple sizes and/or configurations of tools may be provided in a kit. If the improved bone cleaning tool is available as separate and individual tools, the surgeon may request the type of tool that will be specialized for the preparation, removal and/or reimplantation of the autograft. Alternatively, if a plurality of improved bone cleaning tools may be provided in a kit, the kit may include a variety of the designs specialized for the desired cutting (fine or gross), grinding, severing, smoothing and/or other actions desired by the surgeon and/or surgeon technologist.

In other alternative embodiments, an improved bone cleaning tool may be used for a variety of other surgical applications that may include the preparation of bone or other anatomical tissues. For example, the surgical application that may be desired may be a procedure performed to prepare vertebral body endplates for interbody fusions. By removing soft tissue without cutting or grinding cortical bone and/or penetrating cancellous bone, the vertebral endplates may be preserved, which can greatly reduce the chance for interbody cage or graft subsidence, a known complication of such surgery. If desired, one embodiment of a device could be designed such that, when operated in a first direction it facilitates in situ bone cleaning of the lamina, facets and spinous process(es), and in a second direction facilitates cleaning of the vertebral endplates for preparation of an interbody graft.

DETAILED DESCRIPTION OF THE INVENTION

In various embodiments, a "bone cleaning tool" or other cutting structure can be designed to include features that may also leverage a surgical drill's bidirectional features, including cutting features on a "reverse" surface of the structure, as well as surfaces that cut or otherwise perform differently depending upon whether the drill is operated in the forward or reverse directions and/or at a specific angle relative to the work piece, which are features that are not utilized by many currently-available drill bits and burrs. In various alternative embodiments, the bone cleaning tool may be reversible, where the bone cleaning tool operating in either direction allows the cutting, severing, smoothing action, and/or combination thereof of soft tissue and/or bone when desired, which may include similar and/or differing cutting types and/or features when operating in opposing directions (i.e., forward and reverse).

In various embodiments, feature(s) may be provided that allow the bone cleaning tool to collect and/or retain morselized tissues when operated in a forward direction, but which does not collect and/or retain such morselized tissues in the reverse direction. Such an arrangement may be particularly useful to a surgeon that is removing soft tissues by operating the tool in the forward direction, and then reversing the drill and using the bone cleaning tool in a reverse direction to morselize bone and/or collect autograft bone for subsequent reimplantation. If desired, such an embodiment could potentially eject and/or release such morselized tissues when operated in a direction opposite to the collection and/or retention direction, which could include collection of such morselized tissues by placing the bone cleaning tool within a container or cup and then operating the tool in the "release" direction, desirably contacting or "splattering" the inside surface of the cup with the collected tissues and potentially cleaning the bone cleaning tool at the same time.

Figure 1:
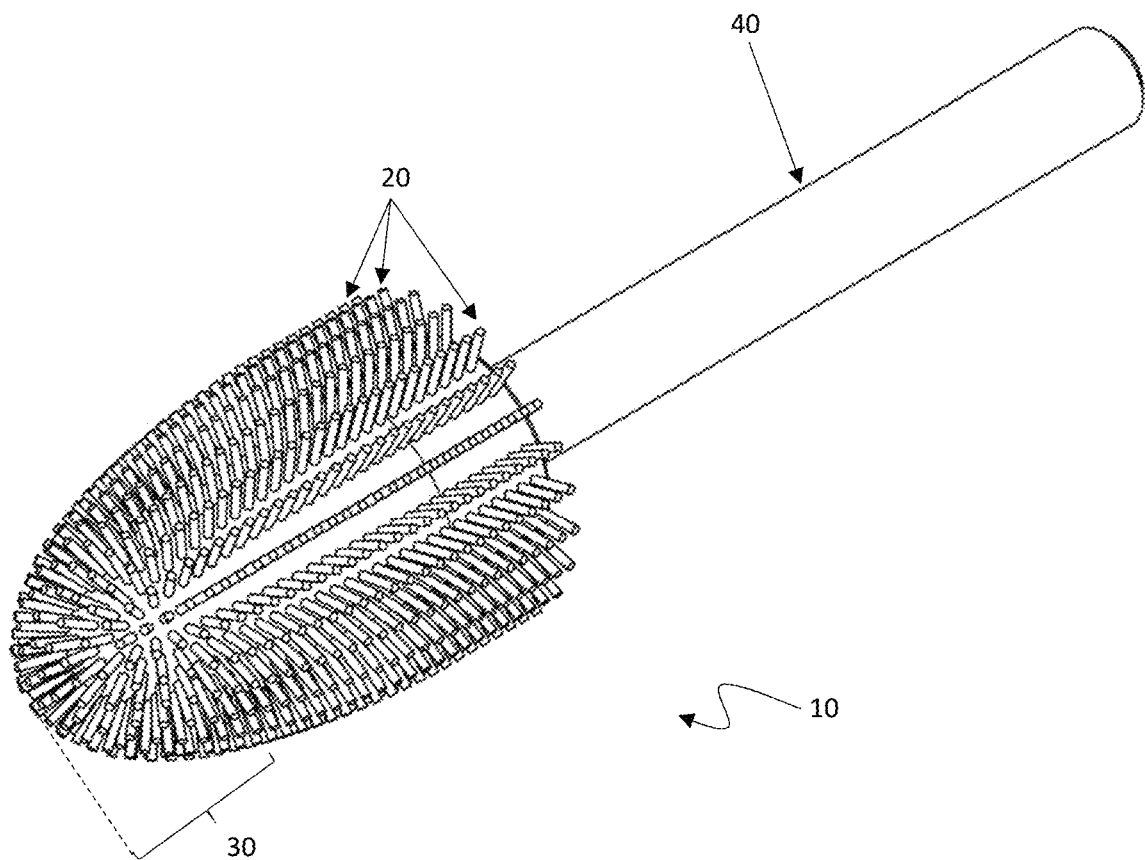
FIG. 1 depicts an isometric view of one embodiment of a bone cleaning tool with extended spines.

FIG. 1 shows one exemplary embodiment of a simple bone cleaning tool head 10 with extended spines 20 and a conical tip to allow access to small and large surfaces. The extended spines may be oriented uniformly, non-uniformly, symmetrical and/or non-symmetrically on the surface of the bone cleaning tool head. In addition, the extended spines may extend orthogonally, perpendicularly, and/or diagonally from the surface of the bone cleaning tool head, which could include spines that are aligned at one or more orientations ranging from parallel to the longitudinal axis of the support shaft up to perpendicular to the longitudinal axis of the support shaft (i.e., including spines oriented at approximately 0°, 15°, 30°, 45°, 60°, 75° and/or 90° from the longitudinal axis of the support shaft)—see FIG. 1. Furthermore, the extended spines may have varying lengths along the surface of the bone cleaning tool head.

In various aspects of the invention, the spines 10 can be attached to and/or formed integrally with the bone cleaning tool head assembly 10. As best seen in FIG. 1, a conical tip 30 of the head 10 can include a plurality of spines which are each aligned approximately perpendicular to a local surface of the curving head, which due to the curvature of the head create a region of non-parallel spines extending outward from the head at the tip 30. Desirably, spines in the tip region can be utilized to cut and/or prepare tissues and/or bone in confined and/or "tight" spaces, with other spines of the head utilized to cut and/or smooth larger portions of the tissues. If desired, some or all of the spines of the tip region could include the same and/or different cutting features than spines of the more flattened region of the head.

The head assembly can be of various diameters and shapes that provide for optional surgical uses. The various components of the bone cleaning tool, including the head assembly, spines and/or solid shaft, can be manufactured from surgical grade stainless steel or other known materials acceptable for use and/or implantation in the human body. Individuals knowledgeable in the art are aware of a variety of materials such as composites, titanium, nitinol, and other alloys which can be used in the manufacture of the current invention.

If desired, the head 10 can be formed from a rigid material, with the spines rigidly fixed to the head, or in alternative embodiments the head could comprise one or more flexible and/or deformable materials, such that the spines could displace and/or flex relative to the head and/or each other during use of the tool. In other alternative embodiments, one or more of the spines may be flexibly attached to a solid and/or flexible head, which could include flexible attachment that allows movement of the spines without allowing for significant rotation of each spine relative to the head, or which allows free rotation of the spines relative to the head but not significant flexing of the spines relative to the head, and/or various combinations thereof. In various embodiments, the spines could be substantially rigid and/or flexible, and could comprise rigid and/or flexible materials and/or combination thereof. If desired, some spines could be flexible and/or flexibly attached, while other spines are rigid and/or rigidly attached to the head, or various combinations thereof.

In the present invention, the bone cleaning tool can include a solid shaft 40 in a plurality of lengths and/or diameters, with the cutting head 10 firmly attached at one end of the shaft. The solid shaft is provided as an interface for inserting the bone cleaning tool or instrument into a surgical rotary hand piece or drill (not shown). The surgical hand piece can be pneumatic, battery or electrically powered, and can provide rotary action, at variable speeds and/or directions, in compliance with the various application methods described herein. Alternatively, a reciprocating or oscillating hand piece (not shown), which could operate in a manner similar to a surgical saw or "saws-all" powered tool (or other type surgical tool), could be utilized with the various embodiments described herein, if desired.

The bone cleaning tool head assembly is desirably firmly attached to the shaft, such that it will rotate at the same revolutions per minute as that of the shaft. When the invention is inserted into a surgical rotary hand piece and the revolutions per minute selected, the bone cleaning tool will desirably rotate at the selected speed. At least one objective of the current invention is that, when the spines of the tool are placed into contact with the soft tissue covering the bone, at least one cutting surface on the spines contact the soft tissue and remove the soft tissue from the surface of the bone without significantly damaging and/or removing the underlying bone.

In at least one embodiment, the bone cleaning tool, after being attached to a surgical rotary hand piece, can be rotated in a circular manner and applied to the soft tissue covering of bone in a back and forth manner, thereby removing the soft tissue from the bone.

Figure 2:
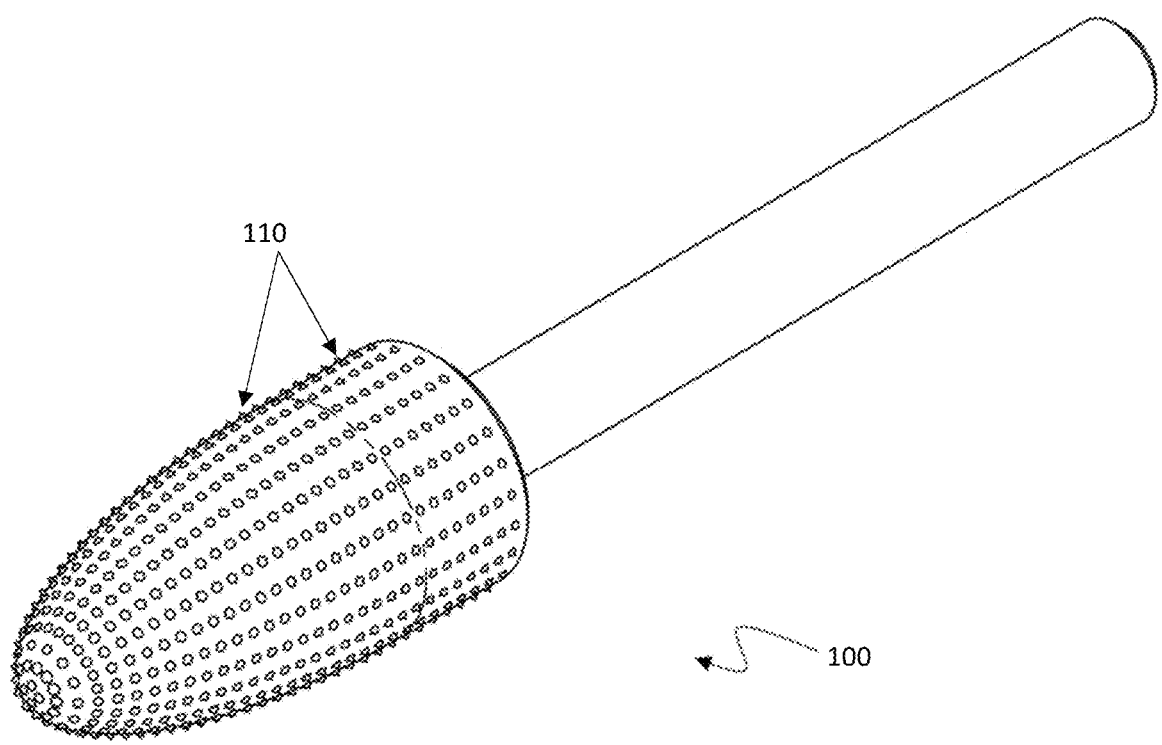
FIG. 2 depicts an isometric view of one embodiment of a bone cleaning tool with low-profile spines.
Figure 3:
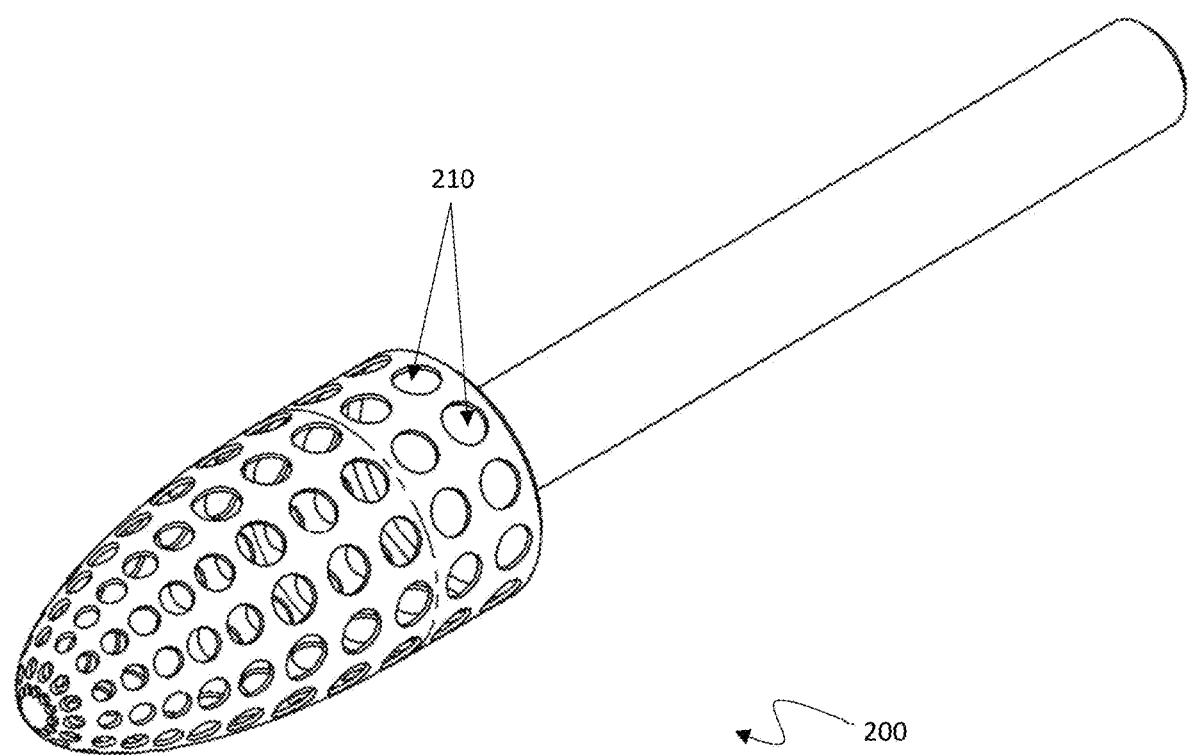
FIG. 3 depicts an isometric view of one embodiment of a bone cleaning tool with apertures.

FIGS. 2 and 3 show exemplary alternative embodiments of bone cleaning tools 100 and 200 incorporating reaming and/or cutting heads that can be utilized to cut out and/or abrade different types and manners of soft and/or hard tissues. The reaming and/or cutting heads 100 and 200 may contain features that facilitate the removal of soft tissue in situ, prior to removal of the bone and potentially preserve and/or prevent damage to remaining bone harvest site area. These features may include textured bone cleaning tool head surfaces including raised protrusions 110 and/or a plurality of apertures 210 placed into and/or on the surface of the reaming and/or bone cleaning tool head. The plurality of apertures 210 and/or raised protrusions 110 may contain one or more cutting surfaces and/or edges in at least one area within and/or surrounding the perimeter of the aperture. For example, an exemplary aperture could include a steeply inclined cutting surface (not shown) formed along one portion of an internal wall (which would desirably cut tissue in a given manner while the tool was rotated in a first direction), and a less-steeply inclined cutting surface (not shown) formed along a second portion of the same internal wall (which would desirably cut tissue in a different manner while the tool was rotated in a second direction). If desired, a first cutting surface could incorporate a more-aggressive cutting surface than the second cutting surface, and/or the first cutting surface could incorporate an edge or contacting surface designed to cut, abrade and/or morselize one type of tissue (i.e., bone) while the second cutting surface could incorporate an edge or contacting surface designed to cut, abrade and/or morselize a second type of tissue (i.e., soft tissue). As used herein, a more-aggressive cutting surface can include surfaces having a sharper edge, a more inclined cutting surface, or some other feature(s) that desirably increases the ability of the more-aggressive cutting surface to cut, abrade and/or morselize a certain type of tissue as compared to another cutting surface type. If desired, the plurality of apertures, textured bone cleaning tool head surface and/or raised protrusions may have similar or different sizes, shapes, cutting edges/features and/or configurations.

If desired, one alternative embodiment of a bone cleaning tool could include three or more cutting surfaces on each spine and/or within each aperture, with a first cutting surface incorporating a less-aggressive cutting surface for use in a forward rotary direction of the tool, a second cutting surface incorporating a more-aggressive cutting surface for use in a reverse rotary direction of the tool, and a third cutting surface incorporating a most-aggressive cutting surface designed for use in a linear, non-rotary manner (i.e., forward planar motion and/or reciprocating back-and-forth motion of the head). If desired, a fourth cutting surface could be further incorporated, such that the reciprocating motion could cut, abrade and/or saw tissue in both back-and-forth directions. Such a tool could be utilized by a surgeon to prepare tissues and/or bone, with different cutting actions performed during (1) forward rotation, (2) reverse rotation and/or (3) linear and/or reciprocating motion of the non-rotating tool, potentially obviating the need for tool exchanges during bone and/or tissue preparation.

Figure 4A:
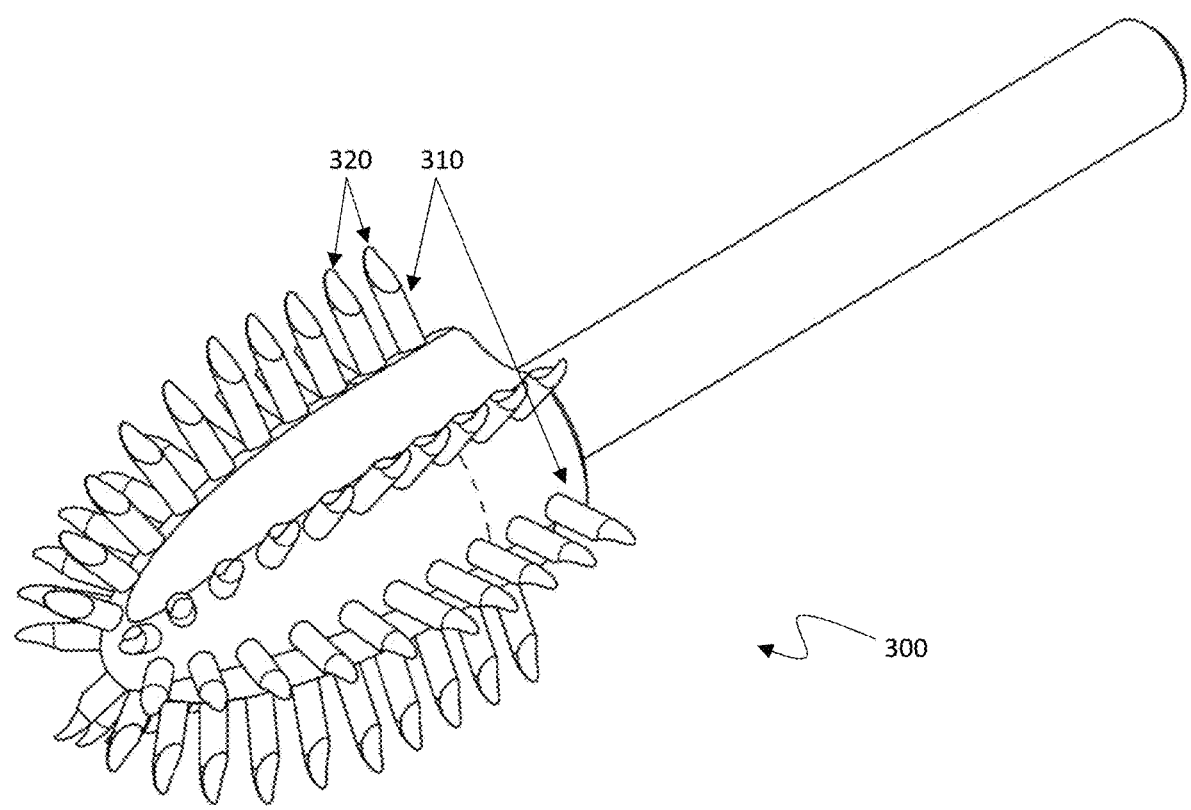
FIGS. 4A-4B depict various exemplary views of one embodiment of a bone cleaning tool with micro-curette surfaces.
Figure 4B:
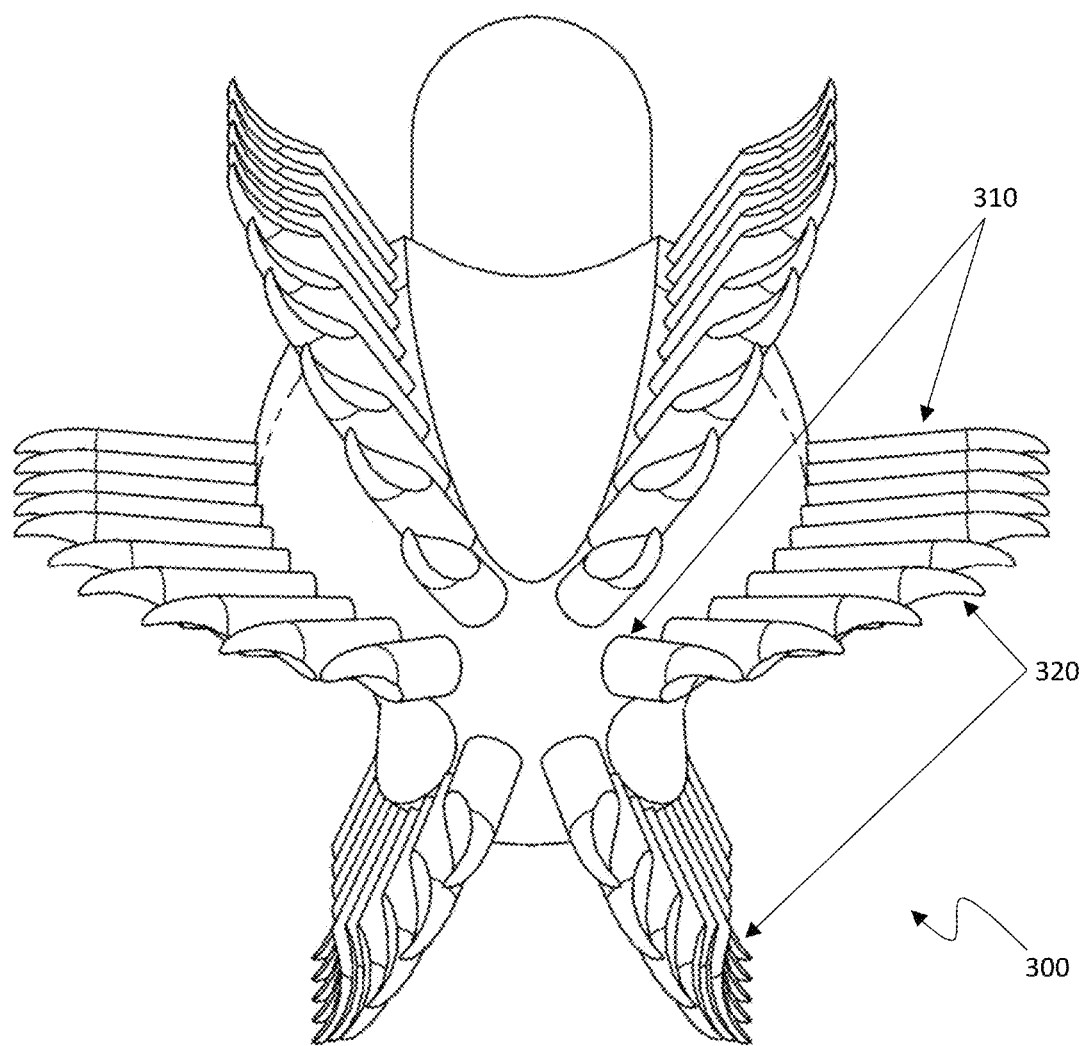
Figure 5A:
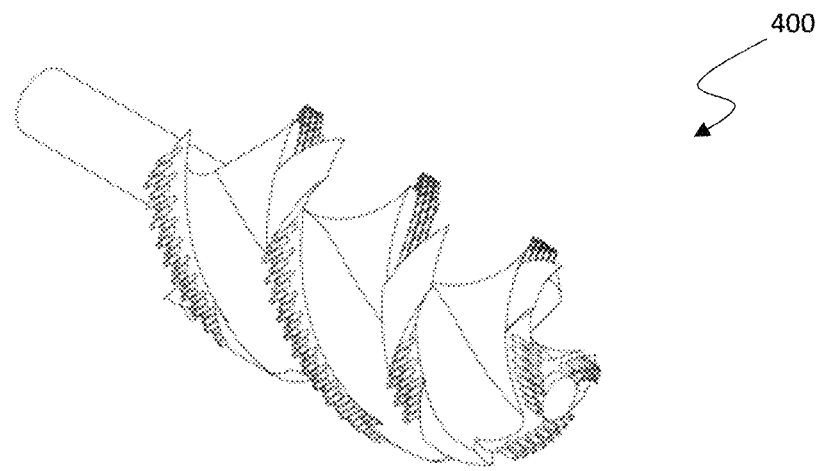
FIGS. 5A-5C depict various exemplary views of one embodiment of a bone cleaning tool with a triple helix flute.
Figure 5B:
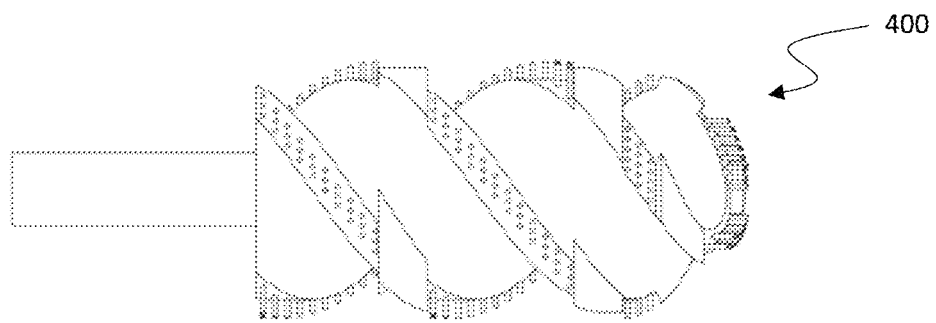
Figure 5C:
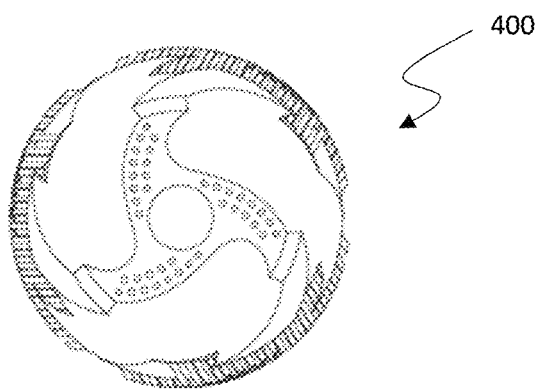
Figure 6A:
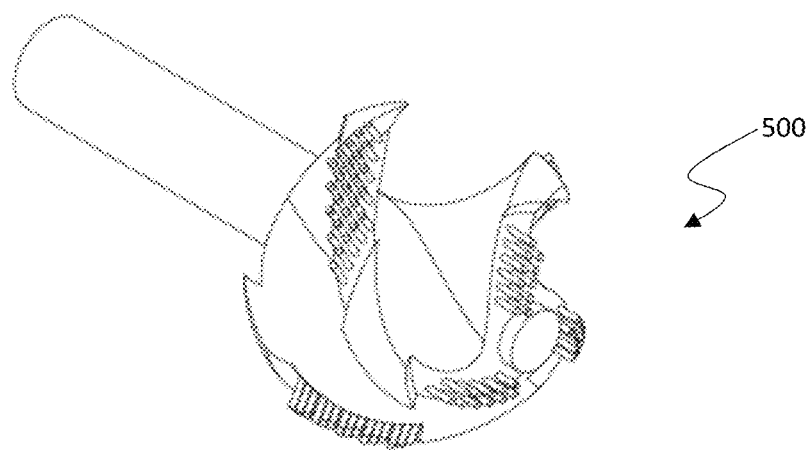
FIGS. 6A-6C depict various exemplary views of one embodiment of a bone cleaning tool with spherical helix flute.
Figure 6B:
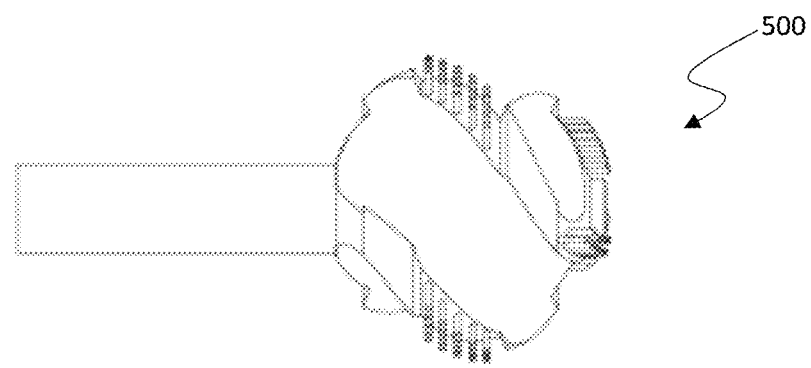
Figure 6C:
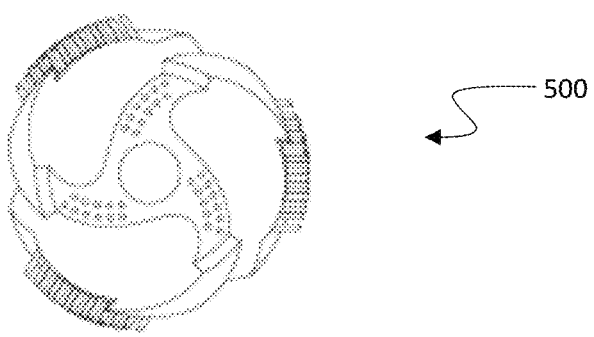

FIGS. 4A and 4B show another alternative embodiment of a bone cleaning tool 300 with spines 310 having spine tips 320 having one or more cutting edges, which in this embodiment are shaped as micro-curettes for a more aggressive scraping force. The micro-curettes can be aligned in various positions and angles to allow for complete soft tissue removal and for using the bidirectional feature of the high-speed drill (i.e., reversibility) for differential cutting/shaping and/or material retention. For example, the spines may be shaped or configured to allow cutting and/or severing of bone or soft tissue in one direction, and when the drill is placed in the reverse direction, the adjacent surface of the spines (and/or the cutting surfaces of opposing-directed spines) may allow grinding and/or smoothing of the bone surface and/or may include an undercut section or void for retention of cut/shaped materials.

FIGS. 5A-5C and 6A-6C show two additional exemplary embodiments of bone cleaning tools 400 and 500 comprising drill bit heads with various "directional cutter" surfaces and/or spines or other protrusions at the head. In these embodiments, the bone cleaning tools can include spines and a helical design with flutes to facilitate egress of soft tissue. The bone cleaning tool head can also include blades which can allow for user-controlled aggressive removal of tougher, more adherent tissue, which may be actuated in a variety of ways, such as by potentially engaging the bone cleaning tool in the reverse direction, so as to allow the cutting surfaces to cut differing amounts and/or types of tissue as compared to the less aggressive "forward" spine direction. In one exemplary embodiment, the spines could be utilized to remove and/or prepare the softer tissues surrounding the bone, while the cutting surfaces and/or blades could be utilized to remove and/or cut the bone, if desired. The bone cleaning tool head may include various shapes, configurations and dimensions to accommodate the size of the bone and/or soft tissue being removed.

Figure 7A:
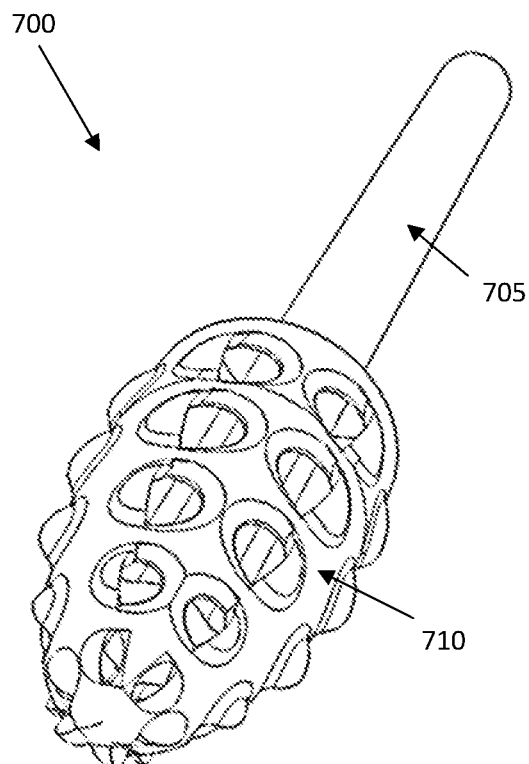
FIGS. 7A through 7E depict various views of another exemplary embodiment of a bone cleaning tool with apertures.

FIG. 7A depicts a perspective view of another exemplary embodiment of a bone cleaning tool 700. The tool 700 includes a drive shaft 705 with a cutting head 710 mounted thereto. As can be best seen in FIG. 7D, the shaft is secured to the cutting head via a plurality of axial supports 715, with three supports 715 depicted in the disclosed embodiment, wherein differing numbers and/or arrangements of supports, such as 2, 4, 5 or 6 supports (or others) can be utilized, if desired. Desirably, the supports 715 can be configured to create one or more openings 720 between the shaft 705 and the cutting head 710, to allow cut and/or abraded material to enter the cutting head after removal from a targeted anatomical region by the tool.

Figure 7B:
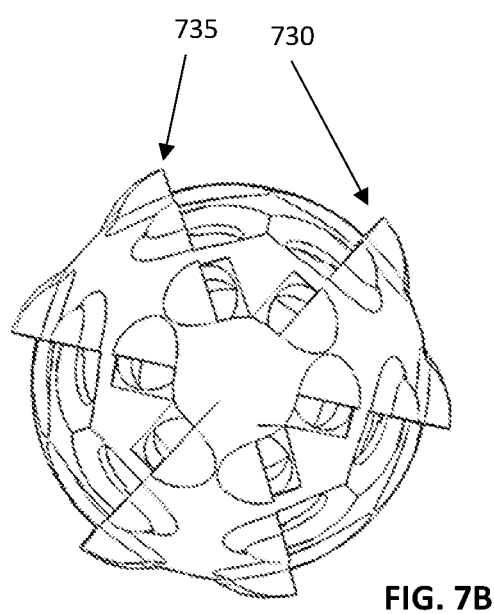
Figure 7C:
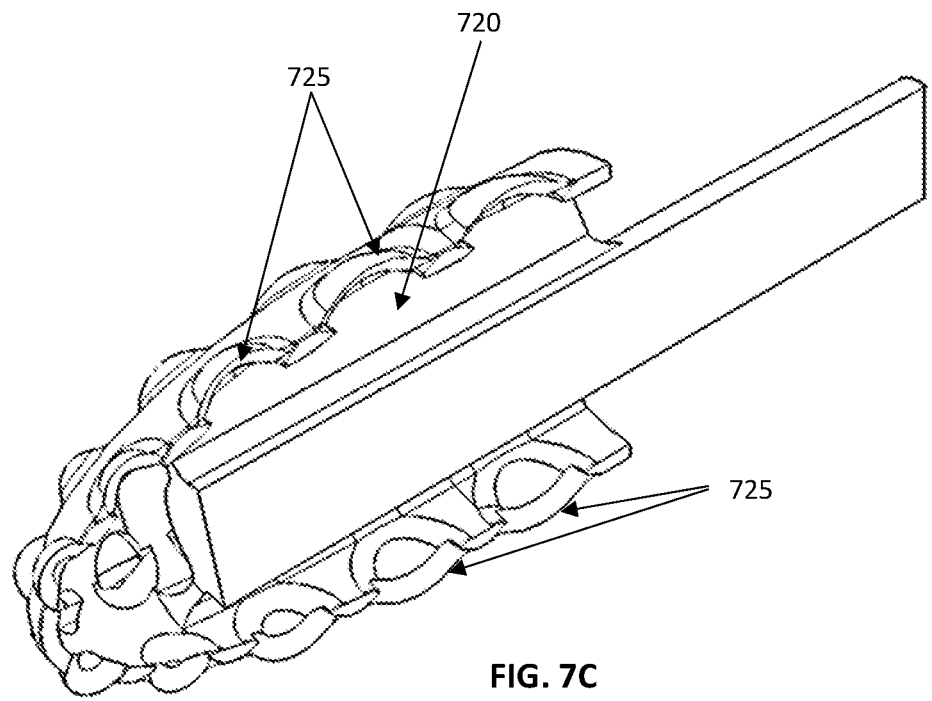
Figure 7D:
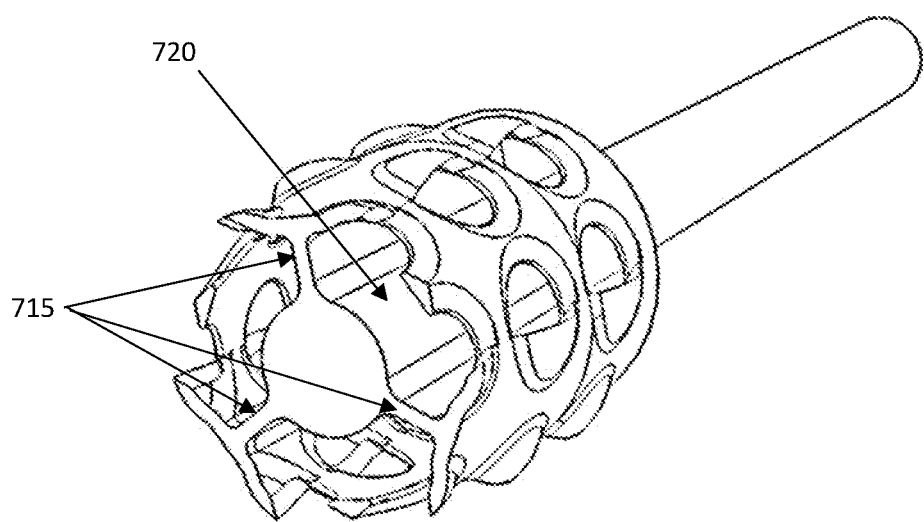
Figure 7E:
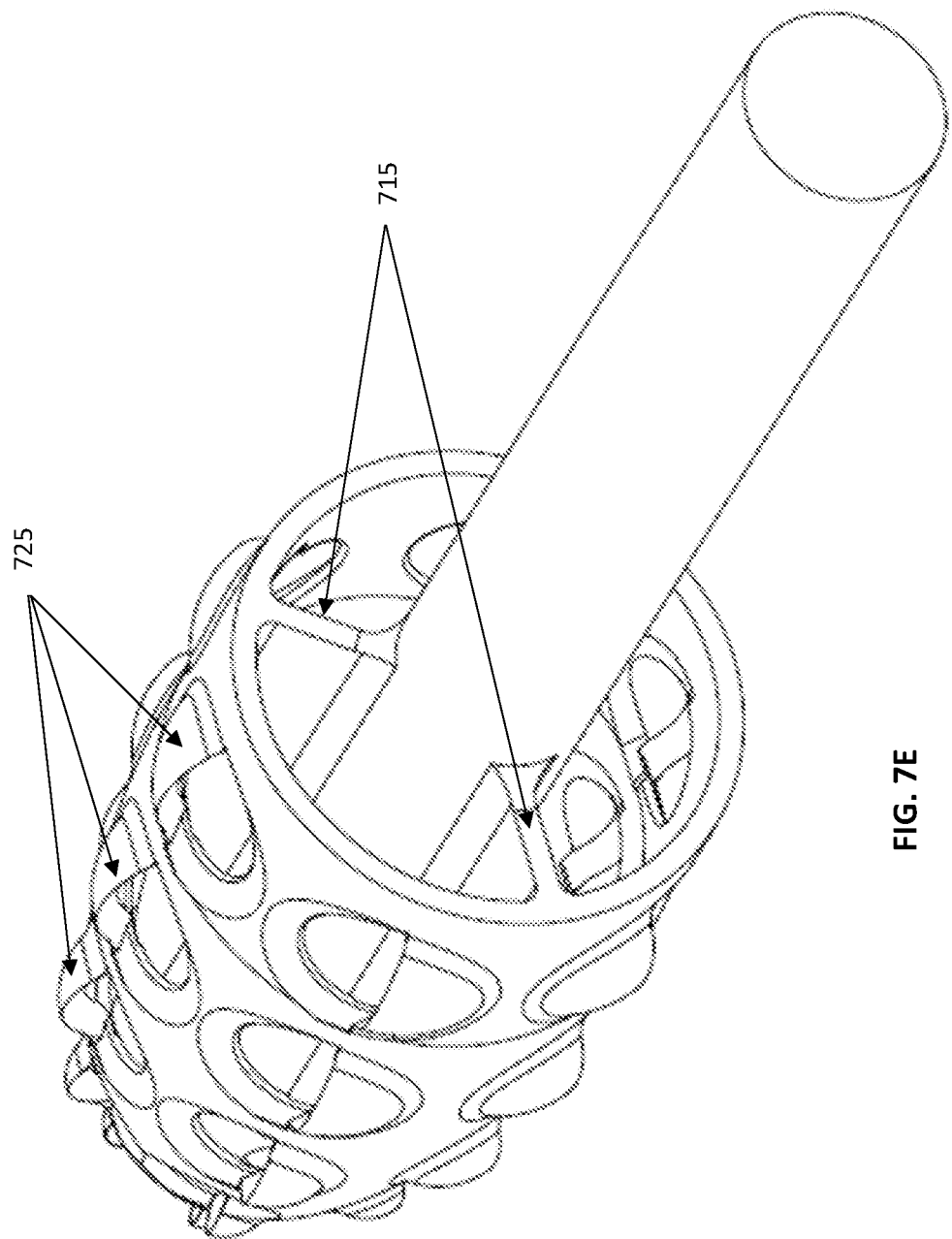

The bone cleaning tool 700 further includes a series of openings formed therethrough, with each opening including at least one cutting or abrading surface or "tooth" 725 therein and/or in close proximity thereto. As best seen in FIG. 7B, a cutting surface can be positioned outward from and/or "proud" of each opening, with various cutting surfaces facing towards differing orientations and/or locations, such as a first set 730 of cutting teeth that face towards a clockwise rotational cutting direction of the tool, and a second 735 set of cutting teeth that face towards a counterclockwise rotational cutting direction of the tool 700. If desired, the first and second sets 730 and 735 of teeth can be designed to cut similar tissues during clockwise and counterclockwise rotation (thereby allowing the tool life to be extended significantly simply by reversing the cutting direction of the tool), and/or the first and second sets of teeth can be designed to cut different types and/or amounts of tissues, depending upon rotational direction (allowing for differential cutting techniques without requiring tool exchanges and/or removal of the cutting tool from the surgical site).

If desired, a single cutting surface can be contained within each opening. Alternatively, one or more openings can included a plurality of cutting surfaces, including cutting surfaces capable of cutting different tissues when the tool is rotated and/or moved in different directions. If desired, additional cutting surfaces could be incorporated into the upper and/or lower surfaces of each opening, including surfaces that cut tissues when the tool is advanced and/or withdrawn along its longitudinal axis.

If desired, one or more of the cutting "teeth" can extend outward of the openings, can be positioned within the openings, and/or could be positioned below the openings. If desired, a single tool could include openings having various combinations and/or orientations of cutting teeth, including a single tool incorporating different sized and/or shape openings and/or different sized, shaped, orientated and/or positioned cutting surfaces relative to the openings (i.e., proud, flush and/or recessed). In addition, the cutting teeth could include cutting surfaces that respond or react to the speed of rotation of the tool, including cutting teeth that may deflect to extend further outward during high-speed rotation (i.e., due to the increased centrifugal force on the teeth as the tool rotates), thereby providing a differential type and/or amount of cutting due to tool rotational speed changes.

Each of the individual cutting surfaces of a given tool can assume a variety of shapes, including flat cutting surfaces as well as curved cutting surfaces and/or more complex cutting surface shapes in two and/or three dimensions. If desired, where multiple cutting surfaces are contained within a single opening, these cutting surfaces could be the same and/or different shapes and/or configurations. In a similar manner, cutting surfaces within each of the plurality of openings within a tool could be the same and/or different configurations in different openings, if desired.

Figure 8A:
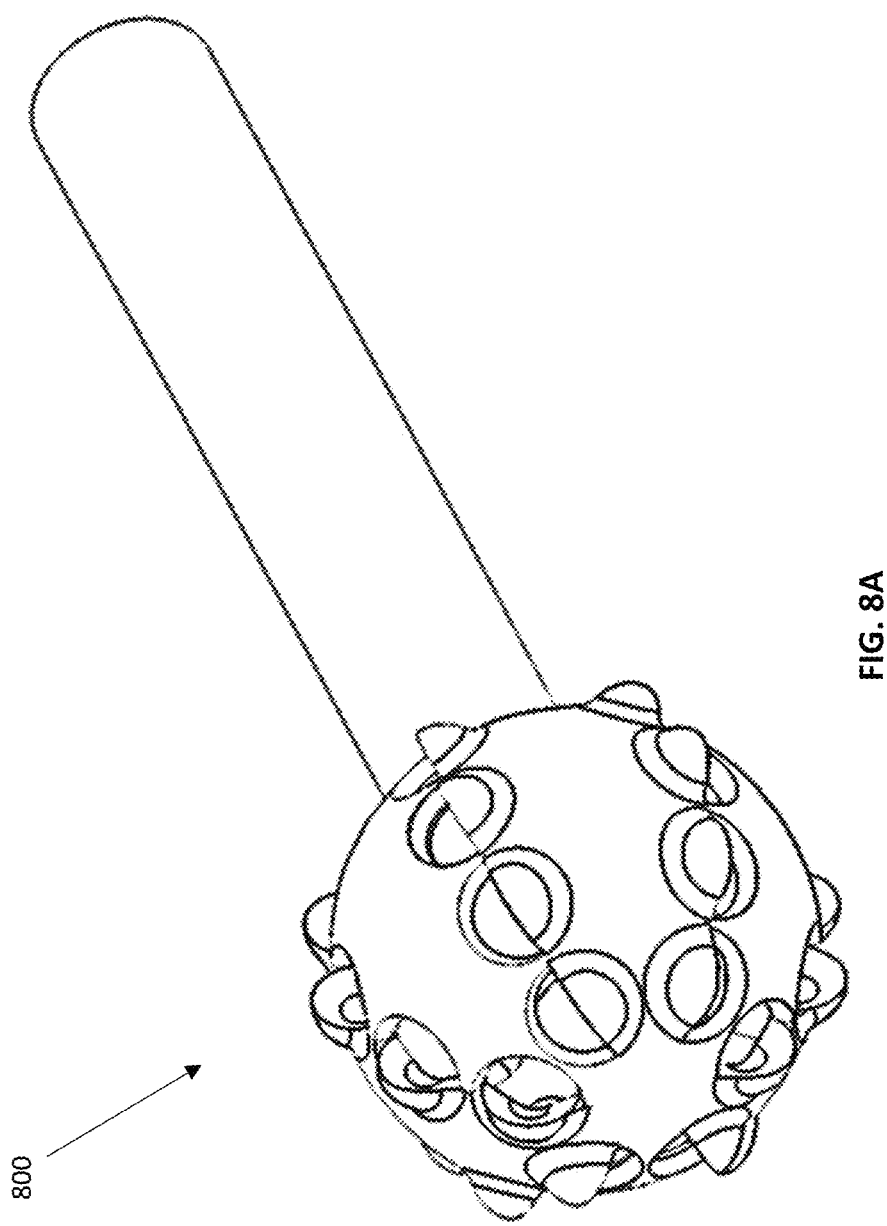
FIGS. 8A and 8B depict perspective views of another exemplary embodiment of a bone cleaning tool with apertures.
Figure 8B:
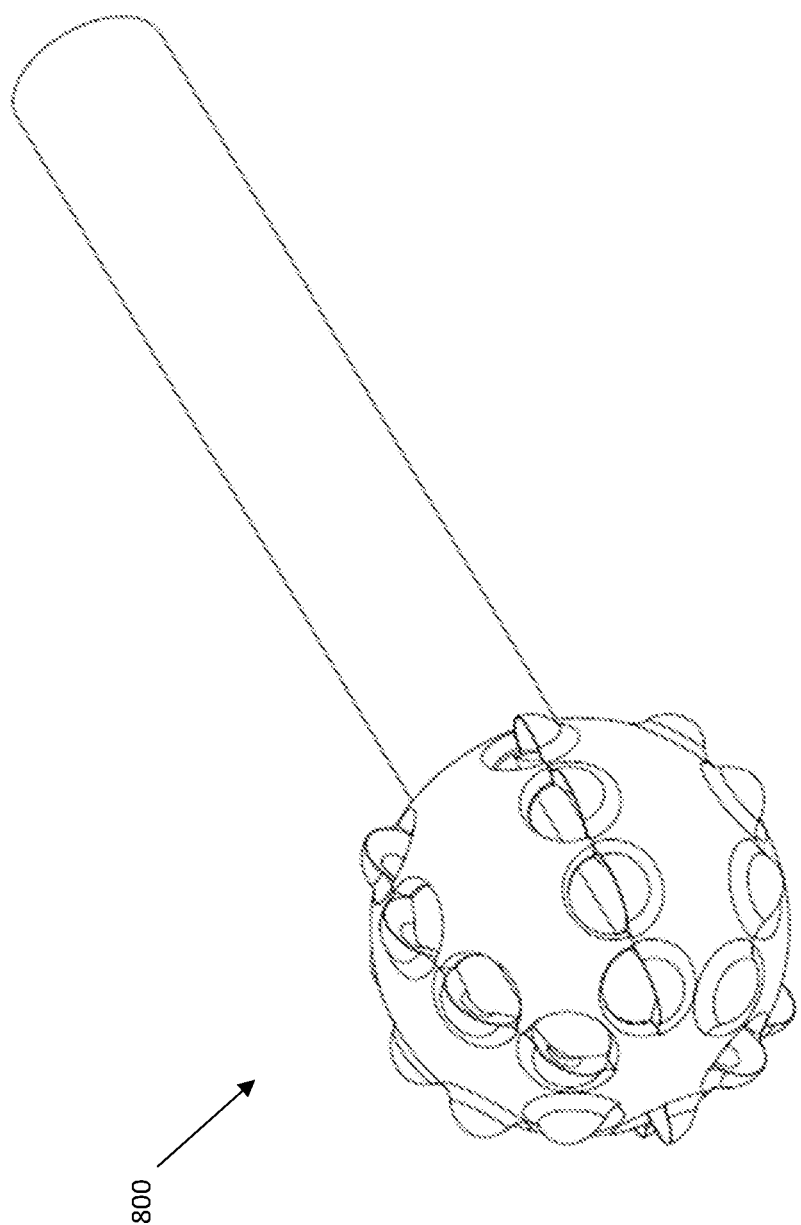

FIGS. 8A and 8B depict another alternative embodiment of a bone cleaning tool 800, in perspective line drawing and shaded formats, respectively. In this embodiment, the outer surface of the tool 800 is generally spherical in shape, with a plurality of outwardly extending cutting surfaces and associated openings. During use, the tool may be rotated, turned and/or otherwise manipulated to present a variety of cutting surfaces towards targeted tissues, which in some embodiments may cut the tissue differentially depending upon the angle and/or speed of the presented cutting surface (s). In a similar manner, the rotation speed of the tool may be varied and/or the rotation may be reversed to present various other cutting surfaces to the tissues of interest. In at least one exemplary embodiment, a plurality of reaming and/or cutting heads can be provided in a kit form, with various tools utilized to cut and/or abrade different types and manners of soft and/or hard tissues. The reaming and/or cutting heads may contain features that facilitate the removal of soft tissue in situ, prior to removal of the bone and potentially preserve and/or prevent damage to remaining bone harvest site area. These features may include textured bone cleaning tool head surfaces including raised protrusions and/or a plurality of openings placed into and/or on the surface of the reaming and/or bone cleaning tool head, with one or more cutting surfaces and/or edges in at least one area within and/or surrounding the perimeter of the openings. For example, an exemplary opening could include a steeply inclined cutting surface formed along one portion of an internal wall (which would desirably cut tissue in a given manner while the tool was rotated in a first direction), and a less-steeply inclined cutting surface formed along a second portion of the same internal wall (which would desirably cut tissue in a different manner while the tool was rotated in a second direction). If desired, the plurality of opening, textured bone cleaning tool head surface and/or protrusions therein may have similar or different sizes, shapes, cutting edges/features and/or configurations In other various embodiments, the bone cleaning tool head may combine the various embodiments as described herein (not shown). For example, the bone cleaning tool head may include apertures with cutting edges in one end of the bone cleaning tool head (i.e., for soft tissue), and have reaming and/or drill bit features near the opposite end (i.e. for bone cutting or rough cuts). Alternatively, the bone cleaning tool head may contain raised protrusions or textured surfaces in one end of the bone cleaning tool head, and have micro-curette shaped spines near the opposite end.

In at least one embodiment, the bone cleaning tool head may be utilized to denude, decorticate and/or shape bone when operating in at least one direction. Desirably, the shaft of the bone cleaning tool head can be placed into a surgical rotary action hand piece and operated in a desired direction at a speed sufficient to complete the removal of soft tissue from an intended bone graft and/or recipient graft site. Following the removal of the soft tissue, the direction of rotation of the bone cleaning tool head can then be reversed and/or otherwise altered (i.e., increased and/or decreased in speed) and then applied to the bone surface so as to contact and remove cortical and/or cancellous bone from the external wall of host and/or graft bone. The rotating spines of the bone cleaning tool head can be lightly applied to the bone (which may be at a higher rate of speed, if desired) and worked in a longitudinal direction along the bone to remove cortical and/or cancellous bone, which may include removal of cortical bone until the soft cancellous bone is visible. If desired, the spines of the bone cleaning tool head can pick-up and/or retain the cortical bone, with the bone tissue extracted as desired.

If desired, the various embodiments described herein can include features that allow a user to contour bone on the graft and/or recipient graft site. The rotating spines of the current invention can desirably be applied to the bone and worked along the bone until the desired shape has been achieved.

In the case of small bone grafts which have already been separated from host tissue, the graft may be held with a bone clamp or other similar instrument and the invention applied to the graft as mentioned herein.

In various embodiment, the bone cleaning tool head may be changed in diameter and/or shape. Accordingly, the materials used to manufacture the bone cleaning tool may be changed or coated with another material. Additionally, the size, shape, diameter, length and/or number of spines may be changed as desired.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A method of preparing a graft bone during a surgical bone graft procedure, the method comprising the steps of:
   providing a rotary cutting tool comprising an elongated shaft and a cutting head including a plurality of openings therein for rotary engagement with a tissue surface of the graft bone, the elongated shaft having a proximal end and a distal end and the cutting head mounted on the elongated shaft proximate to the distal end, at least one of the plurality of openings including a first cutting surface incorporating a contact surface for cutting a softer tissue and a second cutting surface incorporating a contact surface for cutting a harder bony tissue, the first and second cutting surfaces located proximate to an inner wall of the at least one of the plurality of openings;
   causing the rotary cutting tool to rotate in a first direction and applying the rotary cutting tool to the tissue surface to engage with and remove the softer tissue using the first cutting surface; and then causing the rotary cutting tool to rotate in a second direction and applying the rotary cutting tool to the tissue surface to engage with and remove the harder bony tissue using the second cutting surface.

2. The method of claim 1, further comprising the step of:
   causing the rotary cutting tool to rotate in the second direction such that the second direction generally opposes the first direction;
   applying the rotary cutting tool to the tissue surface; and moving the rotary cutting tool along the tissue surface while the rotary cutting tool rotates in the second direction to engage the second cutting surface with a second portion of the tissue surface so as to remove the second portion of the tissue surface.

3. The method of claim 1, wherein the softer tissue comprises a soft tissue surface overlying the harder bony tissue.

4. The method of claim 1, wherein the first cutting surface incorporates a less aggressive cutting surface than the second cutting surface.

5. The method of claim 1, wherein the first cutting surface incorporates a more aggressive cutting surface than the second cutting surface.

6. A method of preparing a graft bone during a surgical bone graft procedure, the method comprising the steps of:
   providing a rotary cutting tool comprising an elongated shaft and a cutting head including a plurality of openings therein arranged for rotary engagement with a tissue surface of the graft bone, the elongated shaft having a proximal end and a distal end and the cutting head mounted on the elongated shaft proximate to the distal end, at least one of the plurality of openings including a first cutting surface incorporating a contact surface for cutting a first tissue and a second cutting surface incorporating a contact surface for cutting a second tissue, the first and second cutting surfaces located proximate to an inner wall of the at least one of the plurality of openings;
   causing the rotary cutting tool to rotate in a first direction at a first rotational speed such that application of the rotary cutting tool to the tissue surface causes the first cutting surface to contact with and remove the first tissue from the graft bone; and then causing the rotary cutting tool to rotate in the first direction at a second rotational speed such that application of the rotary cutting tool to the tissue surface causes the second cutting surface to contact with and remove the second tissue from the graft bone.

7. The method of claim 6, wherein the first tissue comprises a soft tissue surface overlying harder bony tissue.

8. The method of claim 6, wherein the first cutting surface incorporates a less aggressive cutting surface than the second cutting surface.

9. The method of claim 6, wherein the first cutting surface incorporates a more aggressive cutting surface than the second cutting surface.

10. A method of preparing a graft bone during a surgical bone graft procedure, the method comprising the steps of:
    providing a rotary cutting tool comprising an elongated shaft and a cutting head including a plurality of openings therein arranged for rotary engagement with a tissue surface of the graft bone, the elongated shaft having a proximal end and a distal end and the cutting head mounted on the elongated shaft proximate to the distal end, at least one of the plurality of openings including a first cutting surface incorporating a contact surface for cutting a first softer tissue and a second cutting surface incorporating a contact surface for cutting a second softer tissue, the first and second cutting surfaces located proximate to an inner surface of the at least one of the plurality of openings;
    causing the rotary cutting tool to rotate in a first direction and applying the rotary cutting tool to the tissue surface to engage with and remove the first softer tissue using the first cutting surface without cutting an underlying harder bony tissue of the graft bone; and causing the rotary cutting tool to rotate in a second direction and applying the rotary cutting tool to the tissue surface to engage with and remove the second softer tissue using the second cutting surface without cutting the underlying harder bony tissue of the graft bone.

* * * * *